(12) United States Patent
Bratkovski et al.

(10) Patent No.: US 8,477,303 B2
(45) Date of Patent: Jul. 2, 2013

(54) RECONFIGURABLE SURFACE ENHANCED RAMAN SPECTROSCOPY APPARATUS, SYSTEM AND METHOD

(75) Inventors: Alexandre M Bratkovski, Mountain View, CA (US); Wei Wu, Palo Alto, CA (US); Zhiyong Li, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 205 days.

(21) Appl. No.: 13/014,688

(22) Filed: Jan. 26, 2011

(65) Prior Publication Data

US 2012/0188540 A1    Jul. 26, 2012

(51) Int. Cl.
*G01J 3/44* (2006.01)

(52) U.S. Cl.
USPC .......................................................... 356/301

(58) Field of Classification Search
USPC ................................ 356/301, 72–73; 977/902
See application file for complete search history.

(56) References Cited

U.S. PATENT DOCUMENTS

| | | | |
|---|---|---|---|
| 5,250,167 A | | 10/1993 | Adolf et al. |
| 5,532,006 A | | 7/1996 | Lauterbur et al. |
| 6,271,278 B1 | | 8/2001 | Park et al. |
| 6,538,089 B1 | | 3/2003 | Samra et al. |
| 6,615,855 B2 | | 9/2003 | Lopez et al. |
| 7,609,377 B2 | | 10/2009 | Wu et al. |
| 7,790,830 B2 | | 9/2010 | Edmiston |
| 2001/0047054 A1* | | 11/2001 | Zopf et al. .................... 524/815 |
| 2006/0252065 A1 | | 11/2006 | Zhao et al. |
| 2007/0166539 A1 | | 7/2007 | Zhao et al. |
| 2007/0196492 A1 | | 8/2007 | Ito et al. |
| 2010/0038086 A1 | | 2/2010 | Bunnell et al. |
| 2010/0063771 A1 | | 3/2010 | Miyata |
| 2010/0096334 A1 | | 4/2010 | Edminston |
| 2011/0116089 A1* | | 5/2011 | Schmidt et al. ............... 356/301 |

OTHER PUBLICATIONS

Clement Yuen et al., "Surface-Enhanced Raman Scattering: Principles, Nanostructures, Fabrications, and Biomedical Applications," Journal of Innovative Optical Health Sciences, vol. 1, No. 2, 2008, pp. 267-284.
J L Yao et al , "A complementary study of surface-enhanced Raman scattering and metal nanorod arrays," Pure Appl. Chem., vol. 72, No. 1, 2000, pp. 221-228.
Ralph A. Ripp et al., "Novel nanostructures for SERS biosensing," Nanotoday, vol. 3, No. 3-4, Jun.-Aug. 2008, pp. 31-37.
Motofumi Suzuki et al., "In-line aligned and bottom-up Ag nanorods for suriace-enhanced Raman spectroscopy," Applied Physics Letters. vol. 88. 2006. pp. 203121-1 to 203121-3.

* cited by examiner

*Primary Examiner* — Tarifur Chowdhury
*Assistant Examiner* — Abdullahi Nur

(57) ABSTRACT

A reconfigurable surface enhanced Raman spectroscopy (SERS) apparatus, system and method employ a stimulus responsive material to move nanorods of a plurality between inactive and active configurations. The apparatus includes the plurality of nanorods and the stimulus responsive material. The system further includes a Raman signal detector. The method of reconfigurable SERS includes providing the plurality of nanorods and exposing the stimulus responsive material to a stimulus. The exposure causes a change in one or more of a size, a shape and a volume of the stimulus responsive material that moves the nanorods between the inactive and active configurations. The active configuration facilitates one or both of production and detection of a Raman scattering signal emitted by the analyte.

20 Claims, 8 Drawing Sheets

RECONFIGURABLE SURFACE ENHANCED RAMAN SPECTROSCOPY APPARATUS, SYSTEM AND METHOD

CROSS-REFERENCE TO RELATED APPLICATIONS

N/A

STATEMENT REGARDING FEDERALLY SPONSORED RESEARCH OR DEVELOPMENT

N/A

BACKGROUND

Detection and identification (or at least classification) of unknown substances have long been of great interest and have taken on even greater significance in recent years. Among methodologies that hold particular promise for precision detection and identification are various forms of spectroscopy, especially those that employ Raman scattering. Spectroscopy may be used to analyze, characterize and identify a substance or material using one or both of an absorption spectrum and an emission spectrum that results when the material is illuminated by a form of electromagnetic radiation (e.g., visible light). The absorption and emission spectra produced by illuminating the material determine a spectral 'fingerprint' of the material. In general, the spectral fingerprint is characteristic of the particular material facilitating identification of the material. Among the most powerful of optical emission spectroscopy techniques are those based on Raman-scattering.

Raman-scattering optical spectroscopy or simply Raman spectroscopy employs an emission spectrum or spectral components thereof produced by inelastic scattering of photons by an internal structure of the material being illuminated. These spectral components contained in a response signal (e.g., a Raman scattering signal) produced by the inelastic scattering may facilitate determination of the material characteristics of an analyte species including, but not limited to, identification of the analyte. Surface enhanced Raman-scattering (SERS) optical spectroscopy is a form of Raman spectroscopy that employs a Raman-active surface. SERS may significantly enhance a signal level or intensity of the Raman scattering signal produced by a particular analyte species. In particular, in some instances the Raman-active surface comprises regions associated with the tips of nanostructures such as, but not limited to, nanorods. The tips of the nanorods may serve as nanoantennas to concentrate an illumination field to further enhance the strength of the Raman scattering signal.

While SERS and SERS using nanorods may be useful in a wide variety of detection and identification applications, there may be instances that require or at least benefit from being able to enable SERS in a controlled manner. Such controlled enabling may be problematic to implement.

BRIEF DESCRIPTION OF THE DRAWINGS

The various features of examples may be more readily understood with reference to the following detailed description taken in conjunction with the accompanying drawings, where like reference numerals designate like structural elements, and in which.

Figure 1A:
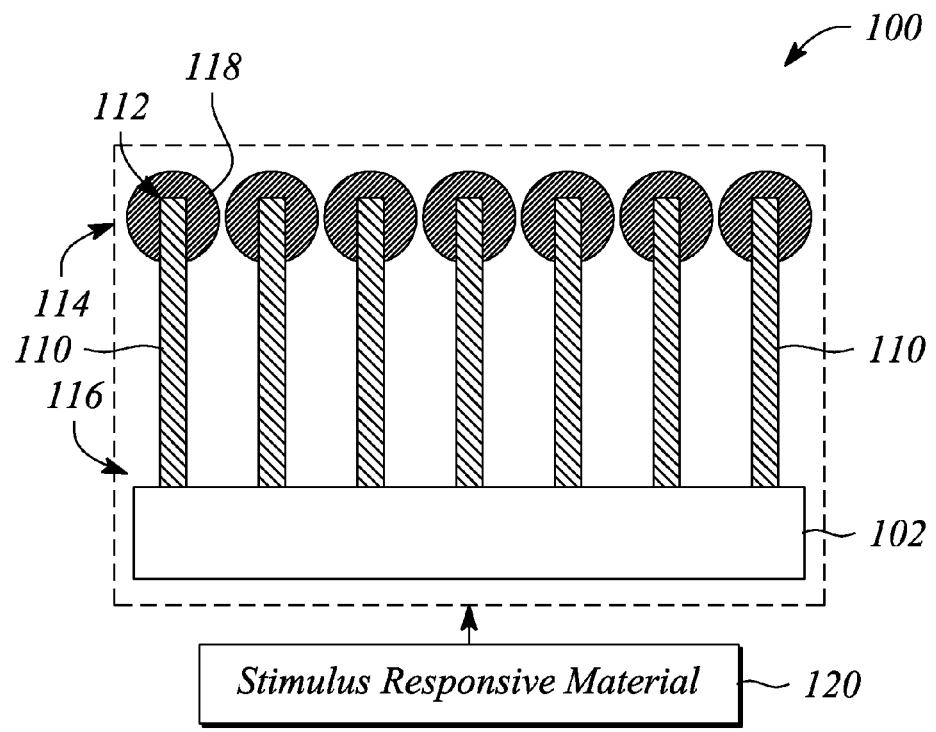
FIG. 1A illustrates block diagram of a reconfigurable surface enhanced Raman spectroscopy (SERS) apparatus, according to an example of the principles described herein.

Certain examples have other features that are one of in addition to and in lieu of the features illustrated in the above-referenced figures. These and other features are detailed below with reference to the preceding drawings.

DETAILED DESCRIPTION

Examples according to the principles described herein facilitate surface enhanced Raman spectroscopy (SERS) employing reconfigurable nanorods. In particular, SERS is performed in conjunction with reconfiguring the nanorods between an inactive configuration and an active configuration, according to the various examples. In the active configuration, one or both of production and detection of a Raman scattering signal from an analyte adsorbed on or closely associated with the nanorods is enhanced and, in some examples, strongly enhanced. Conversely, one or both of Raman scattering signal production and detection may be largely suppressed or substantially inhibited when the nanorods are in the inactive configuration. Furthermore, reconfiguring from the inactive configuration to the active configuration may be performed in a controlled manner. For example, a user may determine when and in some examples, how quickly the reconfiguration occurs. As such, controlled access to or use of the SERS may be provided by the reconfiguration. Moreover, in some examples reconfiguration of the nanorod is reversible. In particular, the reconfiguration providing a transition between the inactive configuration and the active configuration and back again may be repeated many times, according to some examples.

Examples of the principles described herein employ a plurality of nanorods in the active configuration to enhance production and detection of the Raman scattering signal from an analyte. Specifically, an electromagnetic field associated with and surrounding the nanorods (e.g., tips of the nanorods) in the active configuration may enhance Raman scattering from the analyte, in some examples. Further, a relative location of the nanorods or the nanorod tips in the active configuration may provide enhanced Raman scattering. Moreover, an orientation of the nanorods in the active configuration may facilitate detection of the Raman scattering signal, in some examples.

By definition herein, the 'active configuration' is an arrangement, orientation or configuration of the nanorods that facilitates, or in some examples, enhances, one or both of the production and the detection of a Raman scattering signal of an adsorbed analyte. The active configuration may represent one or more of a collective location of the nanorods, a relative position of the nanorods with respect to one another, and an orientation of the tips of the nanorods. The tip orientation may be with respect to one or both of an illumination source configured to stimulate emission of the Raman scattering signal and a detector configured to detect the Raman scattered signal, for example. In contrast, by definition, the 'inactive configuration' is a configuration that may substantially inhibit one or both of the production and the detection of the Raman scattering signal.

When the nanorods are in the active configuration, production of the Raman scattering signal may be enhanced by an order of magnitude or more (e.g., many orders of magnitude) when compared to production while in the inactive configuration, for example. In another example, detection of the Raman scattering signal may be enhanced by an order of magnitude or more when the nanorods are in the active configuration as compared to when the nanorods are in the inactive configuration. In yet another example, the active configuration may independently enhance both the production and the detection of the Raman scattering signal by an order of magnitude or more when the nanorods are in the active configuration as compared to when the nanorods are in the inactive configuration.

In some examples, the active configuration may comprise the tips of the nanorods either touching one another or being immediately adjacent or in close proximity to one another. In these examples, the inactive configuration may comprise the tips being separated from one another sufficiently to render relative inactivity. For example, the tips may be within about 1 nanometer (nm) of one another in the active configuration and separated by more than 10 nm in the inactive configuration. In another example, the tips may be within about 2-3 nm in the active configuration and separated by more than about 10-15 nm in the inactive configuration. In another example, the tips may be separated by more than about 90 percent of a major diameter of the tips in the inactive configuration. For example, the tips may have a diameter that is about 10 nm and the separation may be greater than about 9 nm in the inactive configuration. Conversely, in the active configuration the tips may be spaced apart by less than about 50 percent of the tip diameter (e.g., less than 9 nm). In another example, the tips may be separated by more than about 50 percent of the major diameter of the tips in the inactive configuration while in the active configuration the tips may be spaced apart by less than about 20 percent of the tip diameter. In yet another example, the inactive configuration may comprise the tips being separated by more than about 50 percent of the major diameter of the tips while a separation of less than about 10 percent represents the active configuration. In yet another example, the tips may be substantially touching one another in the active configuration and substantially separated from one another (e.g., separated by more than a major diameter of the tips) in the inactive configuration.

In another example, the active configuration may comprise the tips of the nanorods intersecting an illumination (e.g., an optical beam) from the illumination source of a SERS system while the inactive configuration comprises the tips not intersecting the illumination. In yet another example, an angle between the nanorods and various other elements of the SERS system (e.g., a detector) may facilitate detection of the Raman scattering signal in the active configuration. Conversely, the angle between the nanorods and the other elements may substantially prevent or at least hinder detection in the inactive configuration. Various examples of active and inactive configurations are described in further detail below.

A 'nanorod' herein is defined as an elongated, nanoscale structure having a length (or height) that exceeds by more than several times a nanoscale cross sectional dimension (e.g., width) taken in a plane perpendicular to the length (e.g., length>about 10 times the width). In general, the length of the nanorod is much greater than the nanorod width or cross sectional dimension. In some examples, the length exceeds the cross sectional dimension (or width) by more than a factor of 5 or 10. For example, the width may be about 40 nanometers (nm) and the height may be about 400 nm. In another example, the width at a base of the nanorod may range between about 20 nm and about 100 nm and the length may be more than about a 1 micrometer (µm). In another example, the nanorod may be conical with a base having a width ranging from between about 100 nm and about 500 nm and a length or height that may range between about one and several micrometers.

In various examples, nanorods of the plurality may be grown (i.e., produced by an additive process) or produced by etching or a subtractive process. For example, the nanorods may be grown as nanowires using a vapor-liquid-solid (VLS) growth process. In other examples, nanowire growth may employ one of a vapor-solid (V-S) growth process and a solution growth process. In yet other examples, growth may be realized through directed or stimulated self-organization techniques such as, but not limited to, focused ion beam (FIB) deposition and laser-induced self assembly. In another example, the nanorods may be produced by using an etching process such as, but not limited to, reactive ion etching, to remove surrounding material leaving behind the nanorods. Various techniques used in the fabrication of micro-electromechanical systems (MEMS) and nano-electromechanical systems (NEMS) are applicable to the fabrication of the nanorods and various other elements described herein.

Herein, a 'stimulus responsive material' is defined as a material that changes one or more of size, shape and volume (e.g., specific volume) in response to an externally applied stimulus. In particular, as defined herein, the change in size, shape or volume of the stimulus responsive material when exposed to the applied stimulus is sufficient to move the nanorods between the inactive configuration and the active configuration. In some examples, the change induced in the stimulus response material by exposure to the stimulus results in a change that generally represents more than about 10 percent in one or more of the size, shape or volume of the stimulus responsive material. In some examples, the induced change is more than about 20 percent. In some examples, the induced change is more than about 50 percent. In some examples, the induced change may be greater than about 100 percent (e.g., a doubling in volume).

In some examples, the change may be reversible. In other examples, the change may be substantially permanent. In various examples, the stimulus may include one or more of pH, temperature, an electromagnetic field, a sorbate, a concentration of a substance in a sorbate, and various specific chemical triggers. A 'sorbate', as defined herein, is generally any material that may be taken up by the stimulus responsive material using one or more of absorption, adsorption, or a combination of absorption and adsorption, for example. In some examples, the sorbate is one of water, an aqueous solution, and an organic material. An example of the concentration of a substance in a sorbate includes, but is not limited to, salt concentration or salinity of the sorbate. In some examples, the electromagnetic field includes, but is not limited to, an electric field, a magnetic field, radio frequency (RF) signals, microwave signals and optical signals (e.g., in one or more of the infrared, visible and ultraviolet frequency ranges). In some examples, a specific chemical trigger includes, but is not limited to, glucose, members of a specific binding pair, an enzyme and associated active site, and members of a nucleotide pair.

For example, the stimulus responsive material may comprise a hydrogel or similar super absorbent polymer (SAP). Examples of hydrogels include, but are not limited to, crosslinked polyacrylamides and polyacrylates. A hydrogel may swell when exposed to a sorbate such as, but not limited to water, an aqueous solution, or in some instances, another solvent (e.g., alcohol). The swelling may be the result of absorption of the sorbate (e.g., incorporation of sorbate molecules in a matrix of the hydrogel), in some examples. Moreover, the hydrogel may shrink when the water or another similar sorbate is removed. In some examples, an amount of swelling of the hydrogel, when exposed to the stimulus, is a function of one or more of a hydrophilic/hydrophobic balance of a base polymer, a concentration of cross-linking junctions and a concentration of various counterions that are associated with ionized groups within a matrix of the hydrogel. In other examples, another mechanism such as, but not limited to, hydrogen incorporation in a polymer chain of the hydrogel may be responsible for the one or both of size and volume change. In another example, the stimulus responsive material may comprise a swellable sol-gel. The swellable sol-gel swells when exposed to a non-polar or organic sorbate. A discussion of example swellable sol-gels is provided by Edmiston, U.S. Pat. No. 7,790,830 and by U.S. Patent Application Publication No. 2010/0096334, both of which are incorporated by reference herein. Poly vinyl alcohol-polyacrylic acid arranged in a parallel aggregate has been shown to change length in response to an electric field as disclosed by Adolf et al., U.S. Pat. No. 5,250,167, for example. Moreover, magnetic responsive volume changing gels are disclosed by Lauterbur et al., U.S. Pat. No. 5,532,006, for example. Both of U.S. Pat. No. 5,250,167 and U.S. Pat. No. 5,532,006, are incorporated by reference herein.

Further, as used herein, the article 'a' is intended to have its ordinary meaning in the patent arts, namely 'one or more'. For example, 'a nanorod' means one or more nanorods and as such, 'the nanorod' explicitly means 'the nanorod(s)' herein. Also, any reference herein to 'top', 'bottom', 'upper', 'lower', 'up', 'down', 'front', back', 'first', 'second', 'left' or 'right' is not intended to be a limitation herein. Herein, the term 'about' when applied to a value generally means plus or minus 10%, or within normal tolerances of a measurement technique used, unless otherwise expressly specified. Moreover, examples herein are intended to be illustrative only and are presented for discussion purposes and not by way of limitation.

Figure 1B:
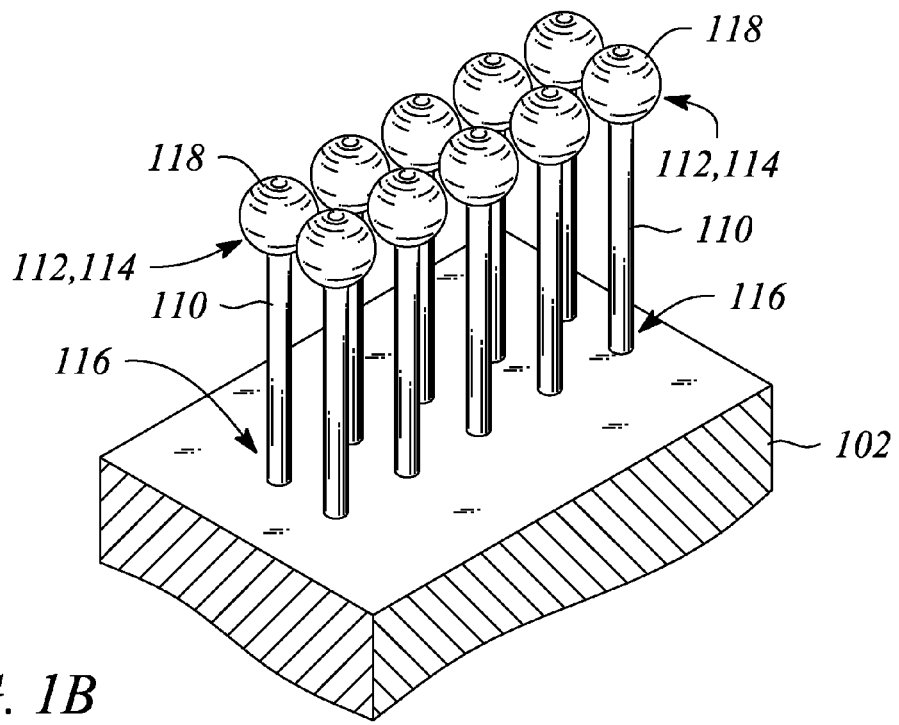
FIG. 1B illustrates a perspective view of a nanorod portion of the reconfigurable SERS apparatus illustrated in FIG. 1A, according to an example.

FIG. 1A illustrates block diagram of a reconfigurable surface enhanced Raman spectroscopy (SERS) apparatus 100, according to an example of the principles described herein. FIG. 1B illustrates a perspective view of a nanorod portion of the reconfigurable SERS apparatus 100 illustrated in FIG. 1A, according to an example of the principles described herein. In particular, the nanorod portion of the SERS apparatus 100 is illustrated on a substrate 102, for example. In some examples, an analyte (not illustrated) may be introduced to and analyzed by the reconfigurable SERS apparatus 100. For example, the analyte may be introduced by flowing a gas or a liquid containing the analyte along or above the substrate 102 that supports the nanorod portion of the SERS apparatus 100. In some examples, the analyte is adsorbed onto a surface of the nanorods. A Raman scattering signal produced by the adsorbed analyte is detected and analyzed to facilitate analysis (e.g., identification of) the analyte, according to various examples.

As illustrated, the reconfigurable SERS apparatus 100 comprises a plurality of nanorods 110 arranged in an array. Each nanorod 110 has a tip 112 at a free end 114 opposite to a fixed end 116 of the nanorod 110 that is supported by the substrate 102. The tips 112 of the nanorods 110 are configured to adsorb an analyte. In some examples, the nanorod 110 is rigidly attached to the substrate 102. In other examples (not specifically illustrated in FIGS. 1A and 1B), the nanorod 110 is indirectly attached to the substrate 102 through an intermediate material or layer, for example.

According to some examples, the tip 112 may either be substantially flattened (as illustrated in FIG. 1A) or have a rounded (i.e., domed) shape. For example, the nanorod 110 may have a tip 112 that results naturally from a process (e.g., VLS growth) used to realize the nanorod 110. In other examples, the tip 112 may be further processed to impart a particular shape to the free end 114 of the nanorod 110. The tips 112 of the nanorods 110 may be flattened using chemical-mechanical polishing, for example.

Figure 2A:
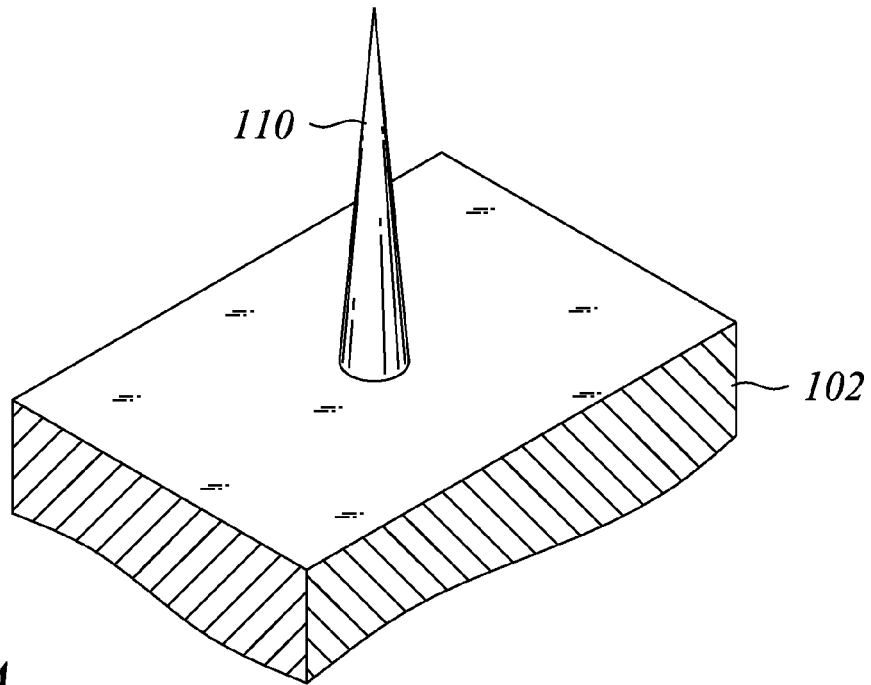
FIG. 2A illustrates a perspective view of a nanorod having a generally tapered shape, according to an example of the principles described herein.

In other examples, the tip 112 is substantially sharp (e.g., as illustrated in FIG. 2A). By 'sharp' it is meant that the tip 112 tapers from a cross sectional size of the nanorod 110 to an edge or a point at an end of the tip 112. The edge or the point generally has a relatively acute angle of inflection between surfaces of the tip 112 leading up to the edge or the point. In other words, a cross sectional size of the tip 112 in a vicinity of the end of the tip 112 (i.e., the edge or the point) is much smaller than an overall cross sectional size of the nanorod 110 away from the tip end. As such, the nanorod 110 having a tip 112 that is substantially sharp distinguishes it from other nanorods 110 having rounded or flat tips.

In some examples, the tip 112 may comprise a nanoparticle 118 attached to the free end 114 of the nanorod 110 (e.g., as illustrated in FIGS. 1A and 1B). In some examples, a material of the nanoparticle 118 may differ from a material of the nanorod 110. In some of these examples, the nanoparticle 118 may be configured to one or both of enhance Raman scattering and facilitate selective analyte adsorption (e.g., by functionalization). In particular, in some examples, the nanoparticle 118 comprises a Raman-active material. For example, the nanoparticle 118 may comprise a Raman-active material such as, but not limited to, gold, silver, platinum, aluminum and copper, having a nanoscale surface roughness, as described further herein.

In some examples, the nanorods 110 have a generally tapered shape compared to that illustrated in FIG. 1B. FIG. 2A illustrates a perspective view of a nanorod 110 having a generally tapered shape, according to an example of the principles described herein. In particular, as illustrated in FIG. 2A, the tapered shape of the nanorod 110 is conical. In other examples (not illustrated), the tapered shape may be generally faceted or pyramidal, for example having three, four, or more facets or sides. In yet other examples, the tapered shape may have a curvilinear perimeter when considering a cross section perpendicular to the long axis of the nanorod 110.

In other examples such as that illustrated in FIG. 1B, the nanorod 110 has a generally columnar shape. The columnar portion may have either curvilinear or faceted perimeter in cross section. In particular, with respect to a cross section taken in a plane perpendicular to the long axis of the nanorod 110 and within the columnar portion, the columnar-shaped nanorod 110 may have a cross section that is characterized by either a curvilinear perimeter or a polygonal perimeter. For example, the columnar-portion may have a triangular cross section, a rectangular cross section or a cross section with more than four sides. In another example, the columnar portion may have a perimeter that is circular, oval or curvilinear (e.g., a square with rounded corners). In some examples (not specifically illustrated), the nanorod may resemble a ribbon (e.g., a rectangular ribbon) having a cross sectional shape with one dimension that is much smaller than another, substantially orthogonal dimension (e.g., a thickness that is much less than a width).

Figure 2B:
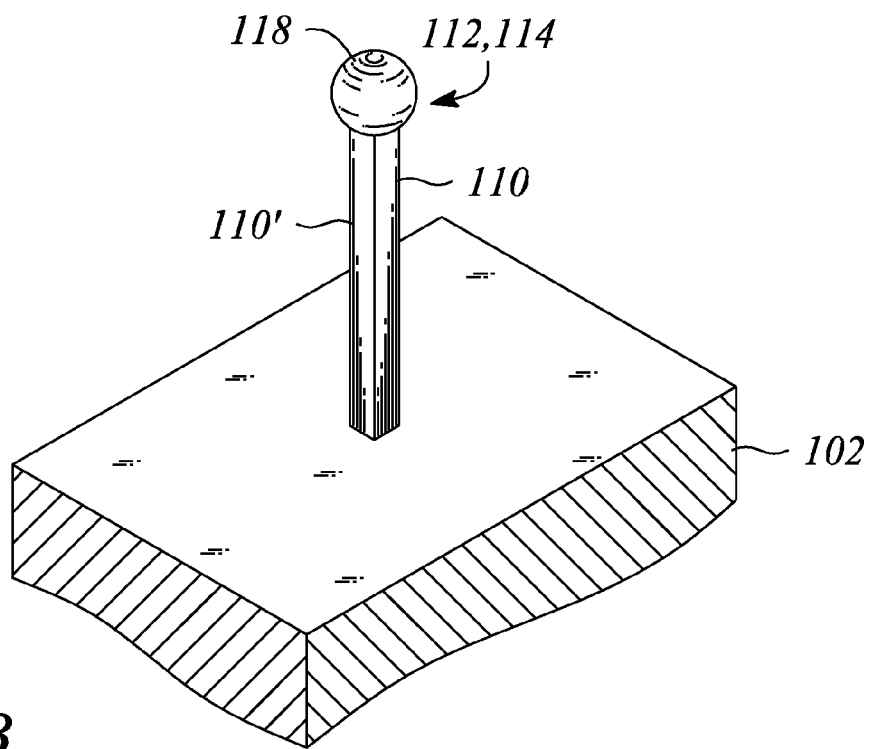
FIG. 2B illustrates a perspective view of a columnar-shaped nanorod, according to another example of the principles described herein.

FIG. 2B illustrates a perspective view of a columnar-shaped nanorod 110, according to another example of the principles described herein. The long narrow shape may facilitate bending the nanorod as is described below. A columnar portion 110' of the columnar-shaped nanorod 110 extends from the substrate to near the tip 112. In the vicinity of the tip 112, the columnar portion 110' is in direct contact with the nanoparticle 118, as illustrated in FIG. 2B. In the example illustrated in FIG. 2B, the columnar-shaped nanorod 110 has a rectangular cross section within the columnar portion 110' while the nanoparticle 118 has a generally rounded shape (e.g., spherical).

The nanorod 110, whether tapered or columnar, generally has a long narrow profile that extends up from the support point at the substrate 102. In particular, the nanorod 110 may be greater than about 5 times longer than it is wide (or thick), according to some examples. In some examples, the nanorod 110 may be at least five times to ten times longer than it is wide. For example, the nanorod 110 may have a width between several nanometers (nm) and about 100 nm and a length that is between about 500 nm and about 1 micrometer (μm).

In some examples, the nanorod 110 comprises a Raman-active material. By definition herein, a Raman-active material is a material that facilitates Raman scattering and the production or emission of a Raman scattering signal from an analyte adsorbed on or in a surface layer of the material during Raman spectroscopy. As mentioned above, examples of Raman-active materials include, but are not limited to, gold, silver, platinum, and other noble metals as well as aluminum and copper. In some examples, the Raman-active materials comprise a layer or layers having nanoscale surface roughness (e.g., generally coated with metal). Nanoscale surface roughness is generally provided by nanoscale surface features on the surface of the layer(s). Nanoscale surface roughness may be produced spontaneously during deposition of the Raman-active material layer(s) (e.g., gold deposition), for example. In another example, surface roughness may be intentionally induced (e.g., using a laser beam).

In some examples, the nanorod 110 may comprise a semiconductor. For example, the semiconductor may comprise silicon (Si) or germanium (Ge) or an alloy of Si and Ge. In other examples, the semiconductor may comprise gallium arsenide (GaAs), indium gallium arsenide (InGaAs), and gallium nitride (GaN), as well as various other III-V, II-VI, and IV-VI compound semiconductors. In some of these examples, the semiconductor may be doped to render the semiconductor more conductive than an intrinsic or undoped (e.g., unintentionally doped) form of the semiconductor. For example, the Si may be doped with phosphorus (P), an n-type dopant, or boron (B), a p-type dopant, to increase the conductivity of the nanorod.

In some examples, the nanorod 110, or at least a portion thereof, is coated with a layer of the Raman signal enhancing or Raman-active material (not illustrated). For example, the nanorods 110 may be coated with a layer of metal such as, but not limited to, gold, silver, platinum, aluminum or copper, since these metals are know as Raman-active materials in conventional SERS. In some examples, the layer of Raman-active material is relatively thin compared to a width or thickness of the nanorod 110. For example, the Raman-active material layer may have a width that is less than about 1/10 of the width of the nanorod 110. The Raman-active material layer may be about 5 to about 10 nm wide, for example.

In some examples, the Raman-active material layer may be confined to or localized in a vicinity of the tips 112 of the nanorods 110. In particular, the Raman-active material may be localized in areas of the nanorods 110 such as, but not limited to, the tips 112 that may be able to come in contact with similar areas of adjacent nanorods 110. In other examples, the Raman-active material layer may extend along more of a length of the nanorods 110 than just a vicinity of the tip 112. For example, a majority of the length, or in some examples, the entire length, of the nanorods 110 may be coated with the Raman-active material layer, according to some examples. In some examples, the Raman-active material layer (e.g., metal) may be annealed or otherwise treated to increase nanoscale surface roughness of the Raman-active material layer after deposition. Increasing the surface roughness may enhance Raman scattering from an adsorbed analyte, for example. In some examples, the Raman-active material layer comprises a layer or layers of nanoparticles. For example, a monolayer of gold nanoparticles may be used to coat the nanorods 110 and produce the Raman-active material layer. The layer(s) of nanoparticles may provide a nanoscale roughness that enhances Raman scattering, for example. In some examples, the Raman-active layer may additionally coat the nanoparticle 118 attached to the tip 112 of the nanorods 110.

In some examples, a surface of the nanorod 110 may be functionalized to facilitate adsorption of the analyte. For example, the tip 112 or portion of the nanorod 110 in a vicinity of the tip 112 may be functionalized (not illustrated) with a binding group to facilitate binding with a specific target analyte species. A surface of the Raman-active material layer on the nanorod 110 at the tip 112 may be functionalized, for example. In another example, a surface of the nanoparticle 118 attached to the nanorod 110 may be functionalized. The functionalized surface (i.e., either a surface of the nanorod 110 itself or a Raman-active material layer coating on one or both of the nanorod 110 and the nanoparticle 118 attached to the tip 112 may provide a surface to which a particular class of analytes is attracted and may bond or be preferentially adsorbed. The functionalized surface may selectively bond with one or more of protein, DNA or RNA, and various hazardous species, for example.

In some examples, the nanorods 110 of the plurality are arranged in a pair of substantially parallel linear arrays. For example, FIG. 1B illustrates a pair of linear arrays of nanorods 110. In other examples, the array may be a two dimensional (2D) array. For example, 2D arrays may exhibit threefold, four-fold, and even higher levels of symmetry. An example 2D array may have nanorods 110 arranged in equally spaced, linear rows and columns, for example. Another example 2D array may be characterized by a triangular arrangement of the nanorods 110. In yet another example, the 2D array may have nanorods 110 arranged in a substantially random or a substantially disordered array.

Referring again to FIG. 1A, the reconfigurable SERS apparatus 100 further comprises a stimulus responsive material 120. The stimulus responsive material 120 is configured to move the nanorods 110 of the plurality between an inactive configuration and an active configuration. Specifically, the stimulus responsive material moves the nanorods by a change in one or more of a size, shape or volume of the stimulus responsive material. The change is provided in response to a stimulus. The active configuration facilitates one or both of production and detection of a Raman scattering signal emitted by an adsorbed analyte in a vicinity of the tips 112 of the nanorods 110.

Figure 3A:
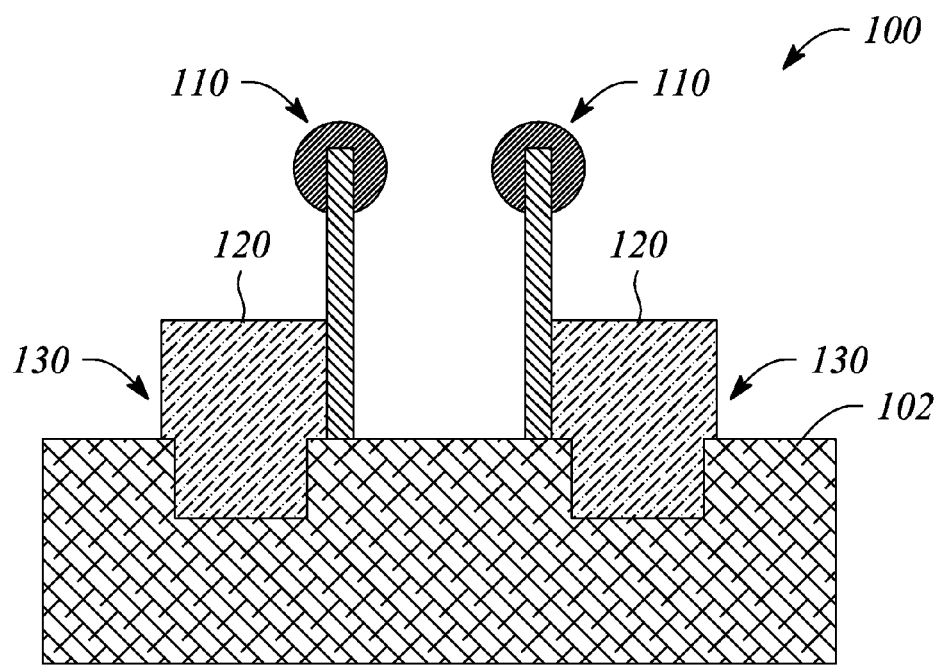
FIG. 3A illustrates a cross sectional view of an example of the reconfigurable SERS apparatus in an inactive configuration, according to an example of the principles described herein.

FIG. 3A illustrates a cross sectional view of an example of the reconfigurable SERS apparatus 100 in an inactive configuration, according to an example of the principles described herein. As illustrated, the example in FIG. 3A depicts a pair of nanorods 100 in the inactive configuration in which the nanorods 110 are substantially separated from one another. The pair of nanorods 110 may be nanorods 110 in two substantially parallel linear arrays, for example.

Also illustrated in FIG. 3A is a stimulus responsive material 120 adjacent to the nanorods 110. In particular, the stimulus responsive material 120 is illustrated adjacent to each nanorod 110 at a nanorod side that faces away from the other nanorod 110. In this example, the stimulus response material 120 is illustrated in a pair of trenches 130 formed in the substrate 102. Further as illustrated, the stimulus responsive material 120 extends above a top surface of the substrate 102. In some examples (not illustrated), the trenches may be omitted and the stimulus responsive material 120 may be affixed to the substrate top surface.

Figure 3B:
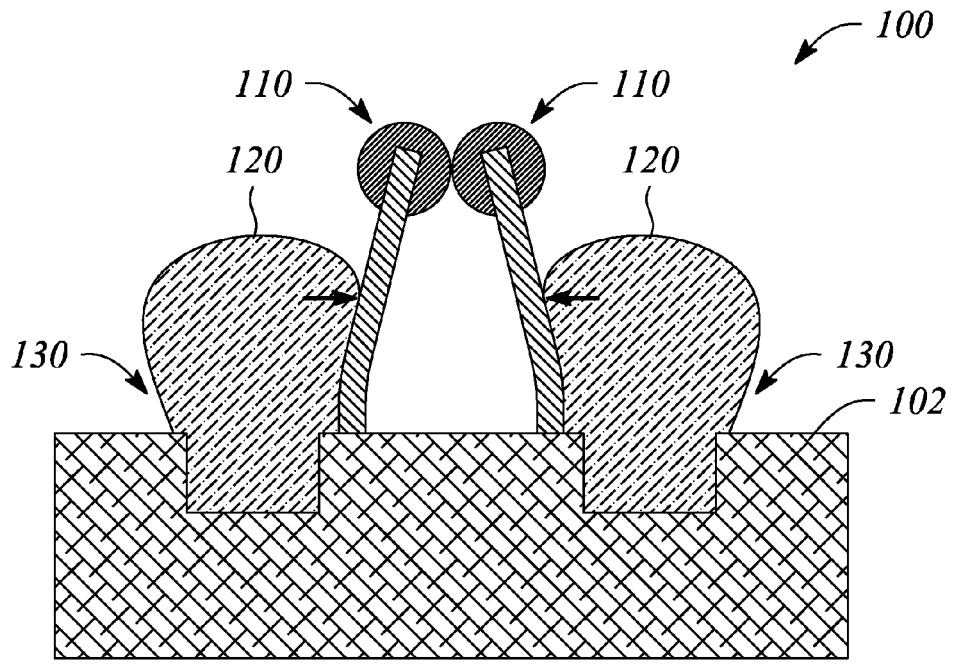
FIG. 3B illustrates a cross sectional view of the reconfigurable SERS apparatus of FIG. 3A following a transition into an active configuration, according to an example of the principles described herein.

FIG. 3B illustrates a cross sectional view of the reconfigurable SERS apparatus 100 of FIG. 3A following a transition into an active configuration, according to an example of the principles described herein. In FIG. 3B, the stimulus responsive material 120 has been exposed to a stimulus. For example, the stimulus may be an appropriate sorbate (e.g., water) and the stimulus responsive material 120 may be a hydrogel. Exposure to the stimulus causes the stimulus responsive material 120 to increase in volume. The increase in volume, in turn, applies a force (e.g., lateral force) to the respective sides of the nanorods 110 as indicated by heavy arrows in FIG. 3B. The applied force bends the nanorods 110 toward one another to achieve the active configuration. For example, the active configuration may be the tips of the nanorods 110 nearly touching one another, as illustrated in FIG. 3B.

Figure 4A:
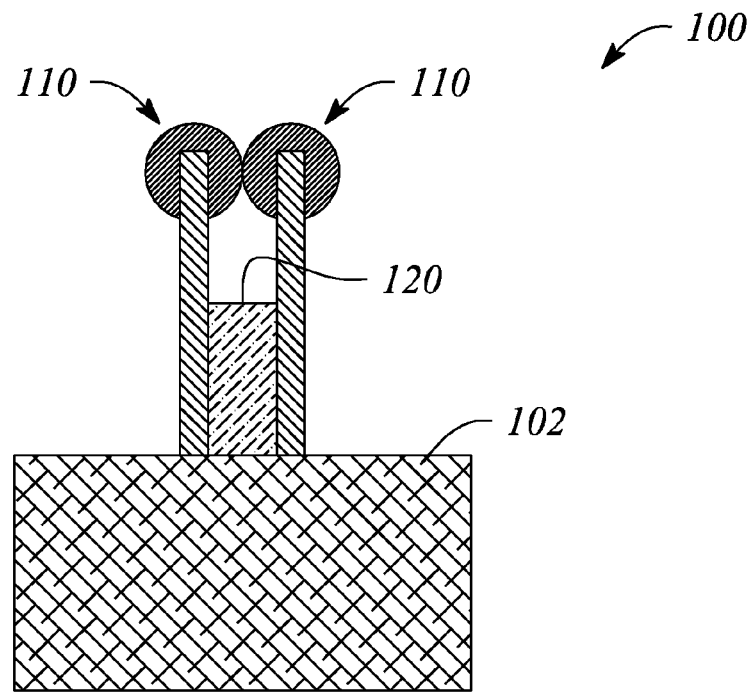
FIG. 4A illustrates a cross sectional view of another example of the reconfigurable SERS apparatus in an active configuration, according to an example of the principles described herein.

FIG. 4A illustrates a cross sectional view of another example of the reconfigurable SERS apparatus 100 in an active configuration, according to an example of the principles described herein. As illustrated in FIG. 4A, the stimulus responsive material 120 is located between the pair of nanorods 110. In some examples (not illustrated in FIG. 4A), the stimulus responsive material 120 may be located in a trench in the top surface of the substrate between the nanorods 110.

Figure 4B:
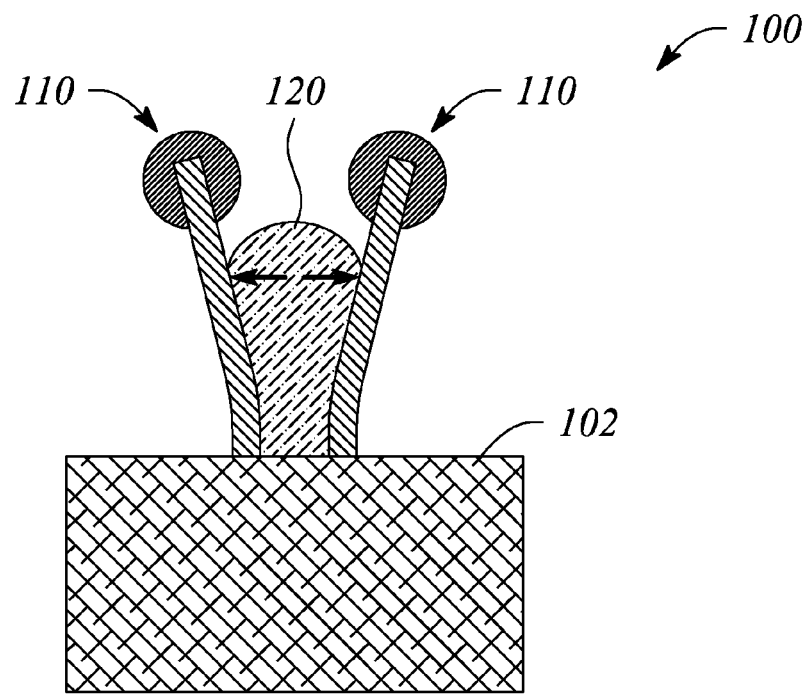
FIG. 4B illustrates a cross sectional view of the reconfigurable SERS apparatus of FIG. 4B in an inactive configuration, according to an example of the principles described herein.

FIG. 4B illustrates a cross sectional view of the reconfigurable SERS apparatus 100 of FIG. 4B in an inactive configuration, according to an example of the principles described herein. As illustrated in FIG. 4B, the stimulus responsive material 120 between the nanorods 110 has been exposed to a stimulus to expand the stimulus responsive material 120. A lateral force (illustrated by heavy arrows in FIG. 4B) produced by the expanding stimulus responsive material 120 bends the nanorods 110 to move the nanorods 110 away from one another. The nanorods 110 are substantially pushed apart by the expanding stimulus responsive material 120 into the inactive configuration in FIG. 4B.

In other examples, the active configuration may further comprise the tips 112 of the nanorods 110 being in an optical beam of an illumination source (illustrated in FIG. 8), whether the tips 112 are in contact or not, while in the inactive configuration, the nanorod tips 112 are out of the optical beam. In yet another example, the active configuration may further comprise the tips 112 of the nanorods 110 in a location that enhances collection of a Raman scattering signal by a detector (illustrated in FIG. 8), while in the inactive configuration, the location of the nanorod tips 112 is not enhanced for signal collection. For example, the location may establish a predetermined angle between the detector, an illumination source, and the nanorod tips 112 that facilitates detection of the Raman scattering signal in the active configuration.

Figure 5A:
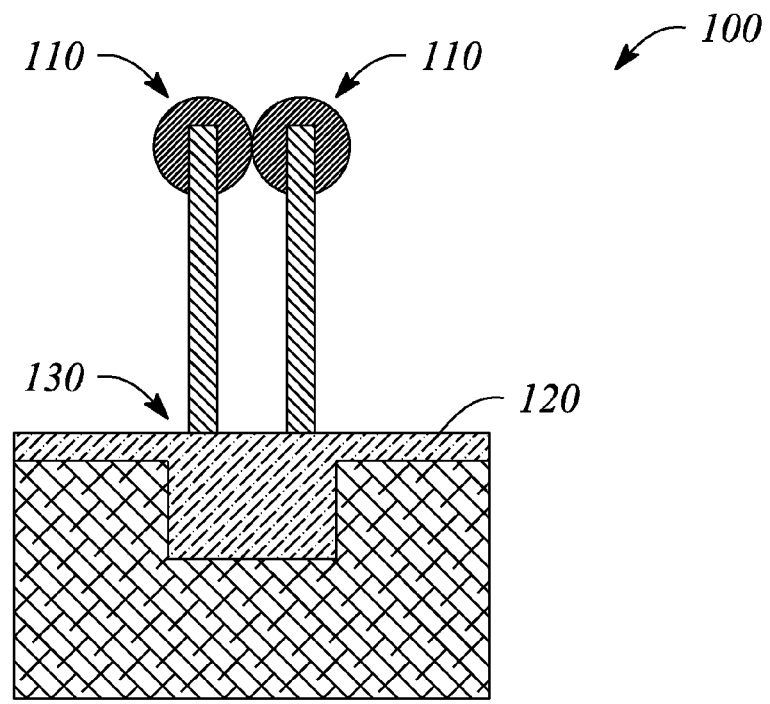
FIG. 5A illustrates a cross sectional view of another example of the reconfigurable SERS apparatus in an active configuration, according to an example of the principles described herein.

FIG. 5A illustrates a cross sectional view of another example of the reconfigurable SERS apparatus 100 in an active configuration, according to an example of the principles described herein. In particular, the stimulus responsive material 120 comprises a layer on the substrate 102 with the nanorods 110 of the plurality being attached to a surface of the stimulus responsive material 120 layer, for example. Further illustrated by way of example, is a trench 130 formed in the substrate surface substantially below the nanorods 110. The stimulus responsive material 120 further comprises a portion that fills the trench 130 and is contiguous with the layer. FIG. 5A illustrates the tips 112 of the nanorods 110 in close proximity to one another and the stimulus responsive material 120 prior to exposure to a stimulus in this active configuration, by way of example.

Figure 5B:
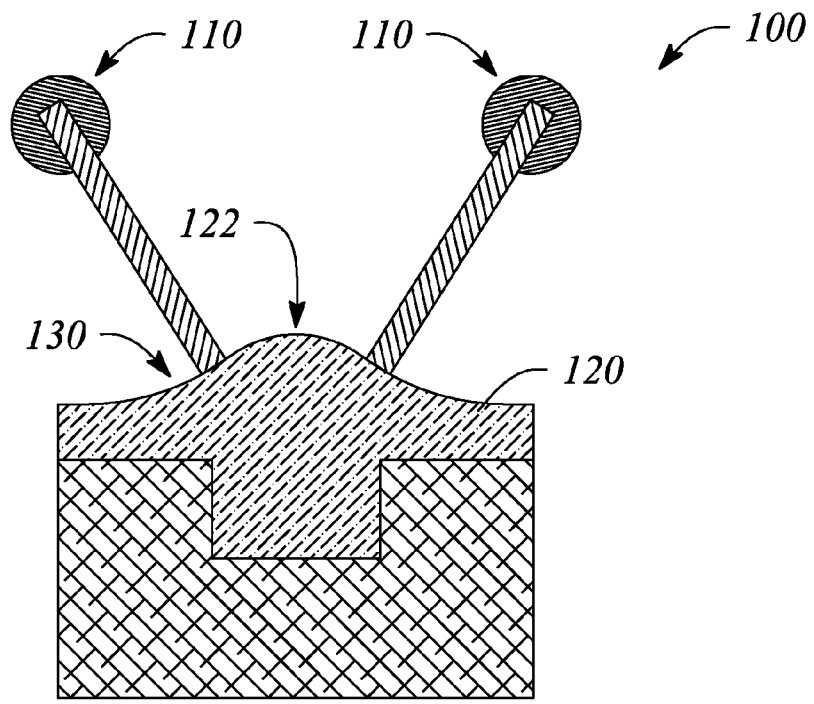
FIG. 5B illustrates a cross sectional view of the example reconfigurable SERS apparatus of FIG. 5A in an inactive configuration, according to an example of the principles described herein.

FIG. 5B illustrates a cross sectional view of the example reconfigurable SERS apparatus 100 of FIG. 5A in an inactive configuration, according to an example of the principles described herein. In particular, the reconfigurable SERS apparatus 100 of FIG. 5B is illustrated after the stimulus responsive material 120 has been exposed to a stimulus that changed the thickness (or volume) of the stimulus responsive material 120. The change in thickness or volume caused the nanorods 110 to move from the active configuration (in FIG. 5A) to the inactive configuration illustrated in FIG. 5B. Specifically as illustrated in FIG. 5B, the stimulus responsive material 120 has expanded or increased in volume to produce a bulge 122 located over the trench 130 and under the nanorods 110. A curvature of a surface of the bulging stimulus responsive material 120 has produced a separation between the nanorods 110, as illustrated. The separation places the nanorods 110 in the inactive configuration. In some examples, the stimulus responsive material 120 exhibits a reversible expansion and contraction as the stimulus is applied and removed. In these examples, a transition between the active configuration and the inactive configuration also may be reversible. In the example illustrated in FIGS. 5A-5B, the trench 130 facilitates production of the bulge 122 that causes the nanorods 110 to separate from one another.

In other examples (not illustrated), the trench 130 may be substantially absent and the thickness change in the stimulus responsive material 120 may simply move the nanorods 110 one or both of up and down without substantially changing a separation therebetween, for example. In some examples, the up and down motion may move the nanorods 110 between the inactive configuration and the active configuration. For example, the thickness change (e.g., expansion and contraction) of the stimulus responsive material 120 may serve to move the tips 112 of the nanorods 110 into and out of an optical beam of an illumination source. In yet another example (not illustrated), the thickness change (with or without the trench 130) may move the nanorods 110 to a location that maximizes collection of a Raman scattering signal by a detector. For example, the location may establish a predetermined geometry (e.g., angle) between the detector, the illumination source and the nanorods 110 that facilitates detection of the Raman scattering signal.

It should be noted that some examples described herein may employ a stimulus responsive material 120 that contracts as opposed to expands in response to a stimulus exposure. For example, the bulge in the stimulus responsive material 120 illustrated in FIG. 5B may be formed into the stimulus responsive material 120 during a manufacturing process and prior to exposure to the stimulus. Exposure to the stimulus may cause the bulge to shrink or contract into the configuration illustrated in FIG. 5A, for example.

Figure 6A:
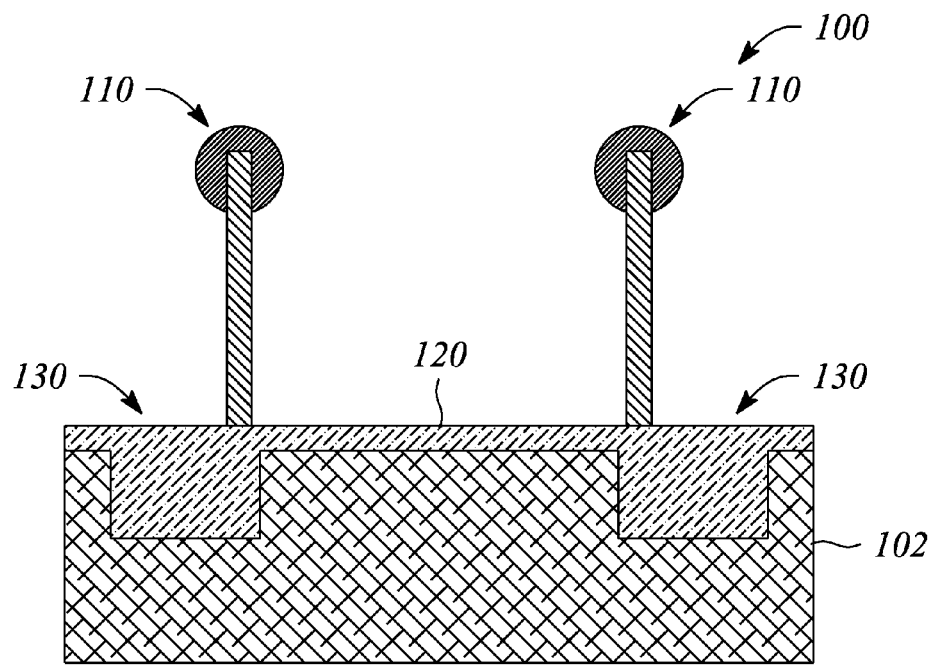
FIG. 6A illustrates a cross sectional view of another example of the reconfigurable SERS apparatus in an inactive configuration, according to an example of the principles described herein.
Figure 6B:
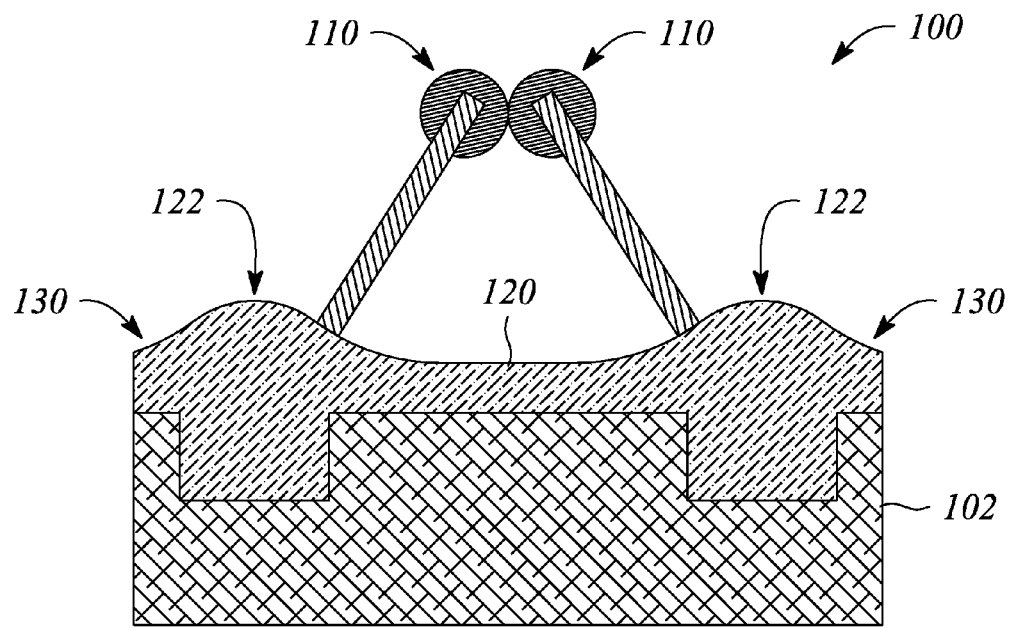
FIG. 6B illustrates a cross sectional view of the example reconfigurable SERS apparatus of FIG. 6A in an active configuration, according to an example of the principles described herein.

FIG. 6A illustrates a cross sectional view of another example of the reconfigurable SERS apparatus 100 in an inactive configuration, according to an example of the principles described herein. FIG. 6B illustrates a cross sectional view of the example reconfigurable SERS apparatus 100 of FIG. 6A in an active configuration, according to an example of the principles described herein. In particular, as illustrated in FIG. 6A, the nanorods 110 are affixed to a surface of a layer of the stimulus responsive material 120 on the substrate 102. Further, the nanorods 110 are located in proximity to a pair of trenches 130 in the substrate 102. The trenches are substantially filled with the stimulus responsive material 120. For example, the nanorods 110 may be located over or adjacent to edges of the trenches 130, as illustrated. As the stimulus responsive material 120 expands, a pair of bulges 122 produced in the stimulus responsive material 120 serves to move the tips 112 of the nanorods 110 closer together. A transition from the inactive configuration of FIG. 6A into the active configuration illustrated in FIG. 6B is provided by the expansion of the stimulus responsive material 120. In the active configuration, the nanorod tips 112 are in closer proximity, and in some examples, may make contact, as illustrated in FIG. 6B.

Figure 7A:
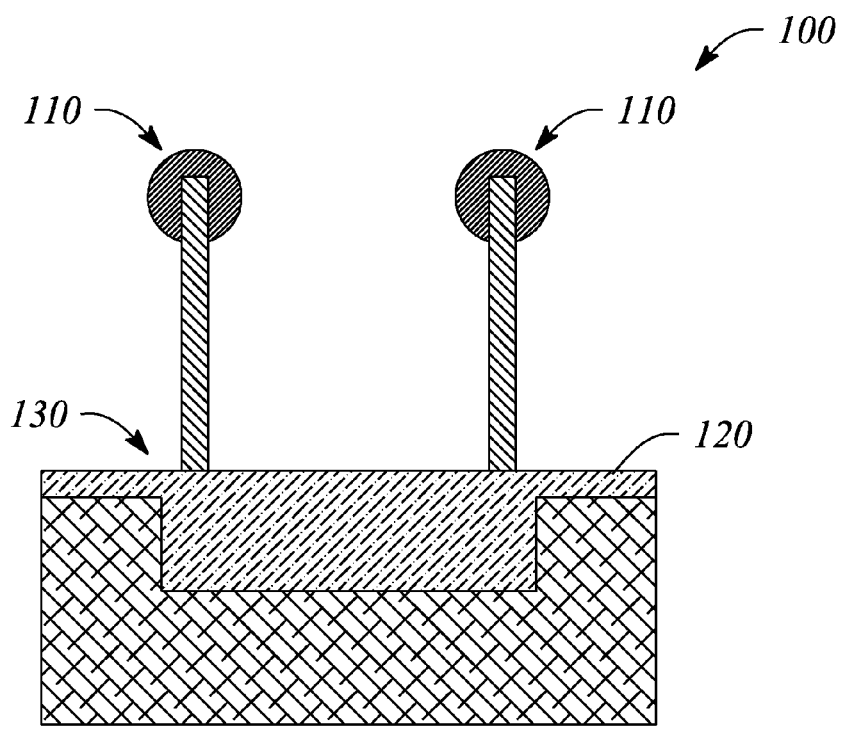
FIG. 7A illustrates a cross sectional view of another example of the reconfigurable SERS apparatus in an inactive configuration, according to an example of the principles described herein.
Figure 7B:
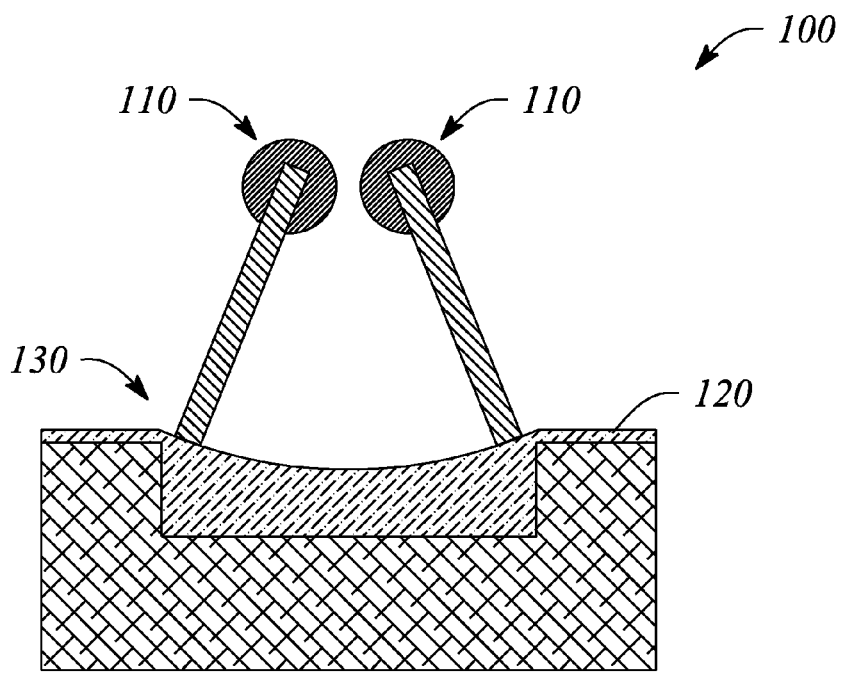
FIG. 7B illustrates a cross sectional view of the example reconfigurable SERS apparatus of FIG. 7A in an active configuration, according to an example of the principles described herein.

FIG. 7A illustrates a cross sectional view of another example of the reconfigurable SERS apparatus 100 in an inactive configuration, according to an example of the principles described herein. FIG. 7B illustrates a cross sectional view of the example reconfigurable SERS apparatus 100 of FIG. 7A in an active configuration, according to an example of the principles described herein. In particular, as illustrated in FIG. 7A, the nanorods 110 are affixed to a surface of the stimulus responsive material 120 on the substrate 102 separated from one another (i.e., in an inactive configuration). Further, the nanorods 110 are located over a trench 130 in the substrate 102. The trench is substantially filled with the stimulus responsive material 120. Moreover, the stimulus responsive material 120 is illustrated prior to exposure to a stimulus.

FIG. 7B illustrates the reconfigurable SERS apparatus 100 after the stimulus responsive material 120 has been exposed to a stimulus. In particular, the stimulus responsive material 120 undergoes a reduction in volume or a contraction when exposed to the stimulus. The contraction forms a depression in a surface of the stimulus responsive material 120 over the trench 130. The depression causes the nanorods 110 to lean toward one another, as illustrated in FIG. 7B. When the tips of the nanorods 110 are in close proximity, the active configuration is provided, for example.

Figure 8:
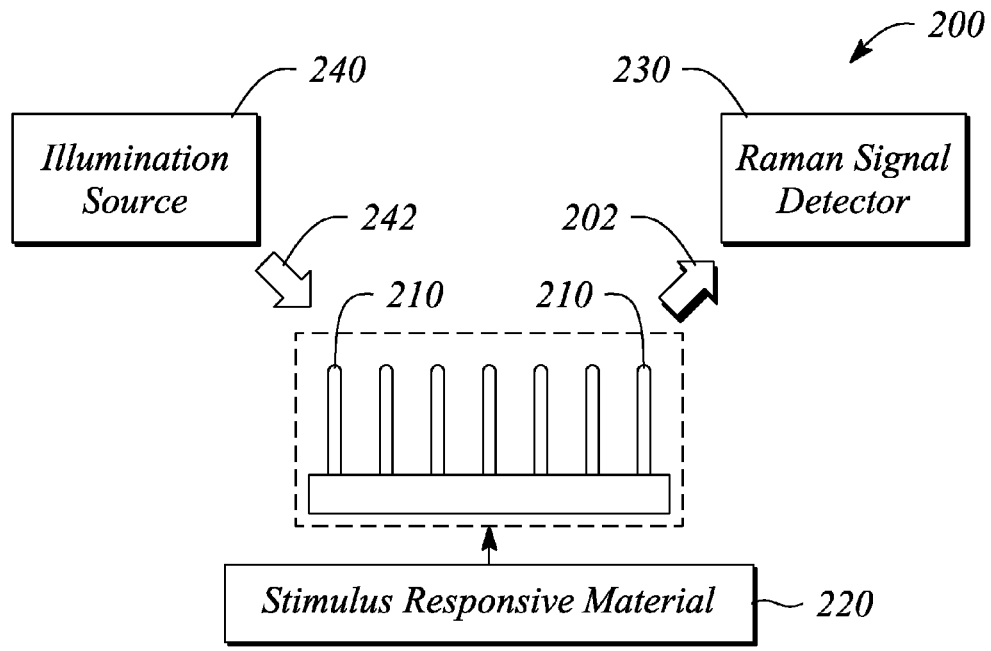
FIG. 8 illustrates a block diagram of a nanorod surface enhanced Raman spectroscopy (SERS) system, according to an example of the principles described herein.

FIG. 8 illustrates a block diagram of a nanorod surface enhanced Raman spectroscopy (SERS) system 200, according to an example of the principles described herein. According to some examples, the reconfigurable SERS system 200 detects and analyzes an analyte using a Raman scattering signal 202 emitted by the analyte. In particular, an active configuration of the reconfigurable SERS system 200 may facilitate detection of the Raman scattering signal emitted by the analyte.

As illustrated in FIG. 8, the reconfigurable SERS system 200 comprises a plurality of nanorods 210 arranged in an array. The array may be a linear array comprising a row of adjacent nanorods 210, for example. In another example, the array may comprise a plurality of rows of nanorods 210 (e.g., a pair of rows). In yet other examples, the nanorods 210 may be arranged in other arrays including, but not limited to, circular arrays and random arrays. Each nanorod 210 has a tip at a free end opposite to an end of the nanorod 210 that is supported by a substrate. The tips of the nanorods 210 are configured to adsorb the analyte, according to some examples.

In some examples, the nanorods 210 are substantially similar to the nanorods 110, described above with respect to the reconfigurable SERS apparatus 100. In particular, in some examples, the nanorods 210 comprise a nanoparticle attached to the tip, the nanoparticle being configured to adsorb the analyte. In some examples, the tips of the nanorods 210 comprise a Raman-active material layer configured to further enhance the Raman scattering signal emitted by the analyte.

The reconfigurable SERS system 200 illustrated in FIG. 8 further comprises a stimulus responsive material 220. The stimulus responsive material 220 is configured to reversibly move the nanorods 210 of the plurality between an inactive configuration and an active configuration. The stimulus responsive material 220 moves the nanorods 210 when exposed to a stimulus. According to some examples, the inactive and active configurations are substantially similar to those described above with respect to the reconfigurable SERS apparatus 100. According to some examples, the stimulus responsive material 220 may be substantially similar to the stimulus responsive material 120 described above with respect to the reconfigurable SERS apparatus 100.

In particular, according to some examples, the active configuration may comprise tips of the nanorods being in close proximity to one another. Further, movement of the nanorods may be reversible by removing the stimulus, for example. In some examples, the stimulus responsive material 220 may comprise a polymer that swells when exposed to a sorbate (e.g., water for a hydrogel). In these examples, the stimulus may comprise the sorbate.

As illustrated in FIG. 8, the reconfigurable SERS system 200 further comprises a Raman signal detector 230. The Raman signal detector 230 is configured to receive the Raman scattering signal 202 from the analyte adsorbed on the tip of the nanorods 210 when the nanorods 210 are in the active configuration.

In some examples, the reconfigurable SERS system 200 further comprises an illumination source 240. The illumination source 240 is configured to illuminate the tips of the nanorods 210. The illumination source 240 may emit an illumination signal 242 comprising a beam of electromagnetic (EM) radiation (e.g., an optical beam or optical signal) having a frequency that stimulates emission of the Raman scattering signal 202 by the analyte, for example. In some examples, the illumination source 240 may comprise a laser and the illumination signal 242 may comprise a laser beam. In other examples, the illumination source 240 may be other means for generating the EM radiation (e.g., a light emitting diode or an incandescent light source).

In some examples, the active configuration further comprises a relationship between a position of the nanorods 210 and the illumination source 240. For example, the active configuration may comprise the tips of the nanorods 210 being positioned to intersect the EM beam (e.g., an optical beam) emitted by the illumination source 240. The inactive configuration may comprise a position of the tips wherein the tips do not intersect the EM beam, for example.

Figure 9:
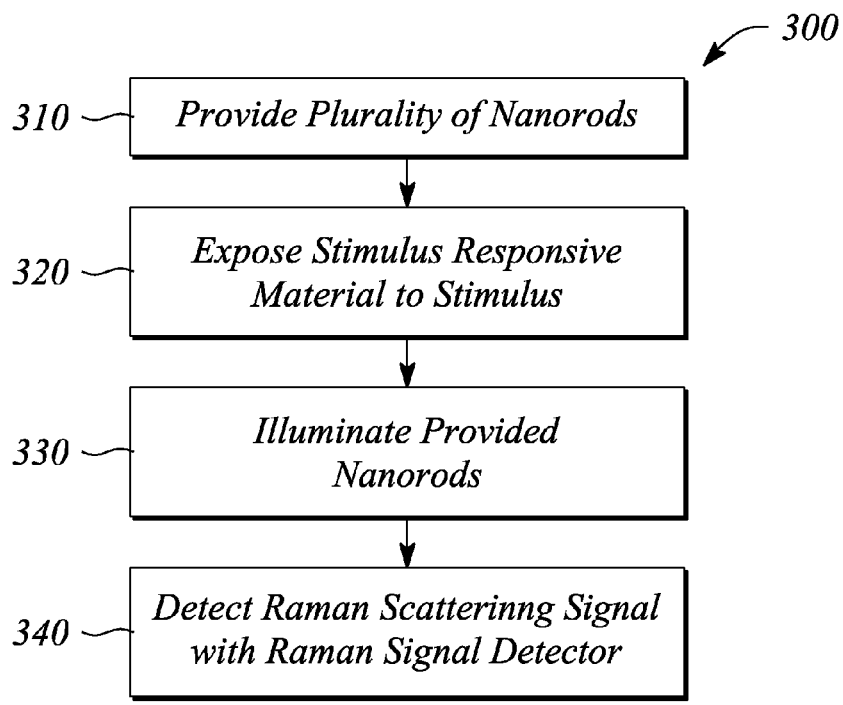
FIG. 9 illustrates a flow chart of a method of reconfigurable surface enhanced Raman spectroscopy (SERS), according to an example of the principles described herein.

FIG. 9 illustrates a flow chart of a method 300 of reconfigurable surface enhanced Raman spectroscopy (SERS), according to an example of the principles described herein. The method 300 of reconfigurable SERS comprises providing 310 a plurality of nanorods. Each nanorod of the plurality has a tip at a free end opposite an end of the nanorod that is supported by a substrate. In some examples, the provided 310 nanorods are substantially similar to the nanorods 110, 210 described above with respect to either of the reconfigurable SERS apparatus 100 or the reconfigurable SERS system 200.

The method 300 of reconfigurable SERS further comprises exposing 320 a stimulus responsive material to a stimulus. The stimulus responsive material is adjacent to the plurality of nanorods, according to various examples. The exposure 320 to the stimulus causes a change in one or more of a shape, a size and a volume of the stimulus responsive material that moves the nanorods of the plurality between an inactive configuration and an active configuration. The active configuration facilitates one or both of production and detection of a Raman scattering signal emitted by an adsorbed analyte.

According to some examples, the method 300 of reconfigurable SERS further comprises illuminating 330 the plurality of nanorods. Illuminating 330 the nanorods produces a Raman scattering signal from an analyte adsorbed on the nanorod, for example at the nanorod tips. In some examples, illuminating 330 the nanorods is provided by an illumination source such as, but not limited to, a laser that produces an optical beam (i.e., an EM beam). According to some examples, the method 300 of SERS employing nanorods further comprises detecting 340 the Raman scattering signal from the adsorbed analyte using a Raman signal detector when the nanorods are in the active configuration. In some examples, the Raman signal detector is substantially similar to the Raman signal detector 240 described above with respect to the reconfigurable SERS system 200.

Thus, there have been described examples of a reconfigurable SERS apparatus, a reconfigurable SERS system and a method of SERS using nanorods that employ a stimulus responsive material to move the nanorods between an inactive configuration and an active configuration. It should be understood that the above-described examples are merely illustrative of some of the many specific examples that represent the principles described herein. Clearly, those skilled in the art can readily devise numerous other arrangements without departing from the scope as defined by the following claims.

What is claimed is:

1. A reconfigurable surface enhanced Raman spectroscopy (SERS) apparatus comprising:
    a plurality of nanorods arranged in an array, each nanorod having a tip at a free end opposite to an end of the nanorod that is supported by a substrate, the tip being configured to adsorb an analyte; and
    a stimulus responsive material to move the nanorods between an inactive configuration and an active configuration, the stimulus responsive material to change in one or more of a size, a shape and a volume in response to a stimulus, the stimulus responsive material being integral with and part of the substrate,
    wherein the active configuration facilitates one or both of production and detection of a Raman scattering signal emitted by the analyte.

2. The reconfigurable SERS apparatus of claim 1, wherein the tips of the nanorods comprises a Raman-active material layer to further enhance Raman scattering from the vicinity of the tips.

3. The reconfigurable SERS apparatus of claim 1, wherein the nanorods further comprise a nanoparticle attached to the tips to adsorb the analyte.

4. The reconfigurable SERS apparatus of claim 3, wherein the active configuration comprises tips of adjacent nanorods being in close proximity to one another, and wherein movement of the nanorods by the stimulus responsive material is reversible.

5. The reconfigurable SERS of claim 1, wherein the stimulus comprises a sorbate, the stimulus responsive material comprising a polymer that swells as the sorbate is taken up by the polymer.

6. The reconfigurable SERS of claim 1, wherein the stimulus responsive material comprises a hydrogel and the sorbate comprises water.

7. The reconfigurable SERS of claim 1, wherein the stimulus responsive material is adjacent to a side of one or more of the nanorods, the change in one or more of the size, the shape and the volume of the stimulus responsive material to apply a force to the side of the nanorod to move the nanorod.

8. The reconfigurable SERS apparatus of claim 1, wherein the nanorods of the plurality are attached to the stimulus responsive material on the substrate, the stimulus responsive material having a thickness that changes in response to the stimulus to move the nanorods between the inactive configuration and the active configuration.

9. The reconfigurable SERS apparatus of claim 8, wherein the thickness change produces a bulge in the stimulus responsive material, the bulge moving the nanorods.

10. The reconfigurable SERS apparatus of claim 1, wherein the stimulus responsive material is between adjacent nanorods, the change of the stimulus responsive material providing a lateral force to the adjacent nanorods that moves the tips of the adjacent nanorods.

11. A nanorod SERS systems comprising the reconfigurable SERS apparatus of claim 1, the nanorod SERS system further comprising:

a Raman signal detector to detect the Raman scattering signal emitted by the analyte when the nanorods are in the active configuration; and an illumination source to illuminate the nanorods, the illumination from the illumination source to produce the Raman scattering signal.

12. The reconfigurable SERS of claim 1, wherein the stimulus responsive material is adjacent to a side of the nanorods, a reversible change in a volume of the stimulus responsive material provided by the stimulus exposure to apply a force to the side of the nanorods to reversibly move the nanorods.

13. A reconfigurable surface enhanced Raman spectroscopy (SERS) system comprising: a plurality of nanorods arranged in an array, each nanorod having a tip at a free end opposite to an end of the nanorod that is supported by a substrate, the tip being configured to adsorb an analyte; a stimulus responsive material to reversibly move the nanorods between an inactive configuration and an active configuration when exposed to a stimulus, the stimulus responsive material being integral with and part of the substrate; and a Raman signal detector to receive a Raman scattering signal emitted by an adsorbed analyte on the nanorod when the nanorods are in the active configuration, wherein the active configuration facilitates detection of the Raman scattering signal.

14. The reconfigurable SERS system of claim 13, wherein the stimulus comprises a sorbate, the stimulus responsive material comprising a material that reversibly swells and contracts as the sorbate is taken up and released by the stimulus responsive material.

15. The reconfigurable SERS system of claim 13, wherein the stimulus responsive material is between adjacent nanorods, a volume change of the stimulus responsive material in response to exposure to the stimulus to provide a lateral force to the adjacent nanorods to move the tips of the adjacent nanorods.

16. The reconfigurable SERS system of claim 13, further comprising an illumination source to illuminate the tips of the nanorods, wherein the active configuration comprises a predetermined position of the nanorods between an initial position and a final position, the active configuration being defined by a predetermined location of the nanorod tips relative to the illumination source.

17. A method of reconfigurable surface enhanced Raman spectroscopy (SERS), the method comprising:

providing a plurality of nanorods in an array, each nanorod having a tip at a free end opposite to an end of the nanorod that is supported by a substrate, the tip adsorbing an analyte; and exposing a stimulus responsive material to a stimulus, wherein exposure to the stimulus changes one or more of a size, a shape and a volume of the stimulus responsive material that moves the nanorods between an inactive configuration and an active configuration, the stimulus responsive material being integral with and part of the substrate, wherein the active configuration facilitates one or both of production and detection of a Raman scattering signal emitted by an adsorbed analyte.

18. The method of reconfigurable SERS of claim 17, wherein a change in volume applies a force to a side of one or more of the nanorods to move the nanorods.

19. The method of reconfigurable SERS of claim 17, wherein the stimulus comprises a sorbate, the stimulus responsive material comprising a polymer that swells when exposed to the sorbate.

20. The method of reconfigurable SERS of claim 17, further comprising:

illuminating the plurality of nanorods to produce the Raman scattering signal from the analyte adsorbed on the nanorod tip; and detecting the Raman scattering signal using a Raman signal detector when the nanorods are in the active configuration.

* * * * *